United States Patent
Nguyen et al.

(10) Patent No.: US 12,391,970 B2
(45) Date of Patent: Aug. 19, 2025

(54) SPATIAL CONTROL OF POLYNUCLEOTIDE SYNTHESIS BY STRAND CAPPING

(71) Applicant: MICROSOFT TECHNOLOGY LICENSING, LLC, Redmond, WA (US)

(72) Inventors: Bichlien Hoang Nguyen, Seattle, WA (US); Jake Smith, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 388 days.

(21) Appl. No.: 17/095,650

(22) Filed: Nov. 11, 2020

(65) Prior Publication Data
US 2022/0145345 A1 May 12, 2022

(51) Int. Cl.
C12P 19/34 (2006.01)
C12N 9/12 (2006.01)
C12Q 1/6874 (2018.01)

(52) U.S. Cl.
CPC ............ *C12P 19/34* (2013.01); *C12N 9/1264* (2013.01); *C12Q 1/6874* (2013.01); *C12Y 207/07031* (2013.01)

(58) Field of Classification Search
None
See application file for complete search history.

(56) References Cited

U.S. PATENT DOCUMENTS

| | | |
|---|---|---|
| 2016/0046974 A1 | 2/2016 | Efcavitch et al. |
| 2019/0062804 A1 | 2/2019 | Church et al. |
| 2019/0112627 A1* | 4/2019 | Arlow ............... C12N 9/1241 |

FOREIGN PATENT DOCUMENTS

| | | |
|---|---|---|
| WO | 2020020608 A1 | 1/2020 |
| WO | 2020120442 A2 | 6/2020 |

OTHER PUBLICATIONS

Egeland, Electrochemically directed synthesis of oligonucleotides for DNA microarray fabrication, Nucleic Acids Research, 33(14): 1-7, 2005. (Year: 2005).*
Ageno, The alkaline denaturation of DNA, Biophys. J., 9(11): 1281-1311, 1969. (Year: 1969).*
"International Search Report & Written Opinion issued in PCT Application No. PCT/US21/052350", Mailed Date: Mar. 7, 2022, 16 Pages.
Barthel, et al., "Enhancing Terminal Deoxynucleotidyl Transferase Activity on Substrates with 3' Terminal Structures for Enzymatic De Novo DNA Synthesis", In Journal of Genes, vol. 11, Issue 1, Jan. 16, 2020, pp. 1-9.
Lee, et al., "Photon-directed Multiplexed Enzymatic DNA Synthesis for Molecular Digital Data Storage", In Journal of BioRxiv, Feb. 20, 2020, pp. 1-24.
Lee, et al., "Terminator-free Template-independent Enzymatic DNA Synthesis for Digital Information Storage", In Journal of Nature Communications, vol. 10, Article No. 2383, Jun. 3, 2019, pp. 1-12.
Chua, et al., "Evolving a Thermostable Terminal Deoxynucleotidyl Transferase", In Journal of ACS Synthetic Biology, Jun. 4, 2020, pp. 1725-1735.
Fernandez-Garcia, et al., "Selective Acylation of Nucleosides, Nucleotides and Glycerol-3-phosphocholine in Water", In Journal of Synlett, vol. 28, Issue 1, Oct. 11, 2016, 5 Pages.

* cited by examiner

*Primary Examiner* — Gary Benzion
*Assistant Examiner* — Carolyn L Greene
(74) *Attorney, Agent, or Firm* — Benjamin Keim; Newport IP, LLC

(57) ABSTRACT

Enzymatic polynucleotide synthesis with a template-independent polymerase is used to create multiple polynucleotides having different, arbitrary sequences on the surface of an array. The array provides a spatially-addressable substrate for solid-phase synthesis. Blocking groups are attached to the 3' ends of polynucleotides on the array. Prior to polynucleotide extension, the blocking groups are removed at a selected location on the array. In an implementation, the blocking groups are acyl groups removed with a negative voltage created at an electrode. The array is then incubated with the polymerase and a single species of nucleotide. Nucleotides are incorporated onto the 3' ends of the polynucleotides without blocking groups. Washing removes the polymerase and free nucleotides. To create polynucleotides with different sequences at different locations on the array, the location where the blocking groups are removed and the species of nucleotide may be changed during repeated cycles of synthesis.

15 Claims, 4 Drawing Sheets

SPATIAL CONTROL OF POLYNUCLEOTIDE SYNTHESIS BY STRAND CAPPING

BACKGROUND

Synthetic oligonucleotides, also referred to as polynucleotides, such as deoxyribonucleic acid (DNA) and ribonucleic acid (RNA) have uses in medicine, molecular biology, nanotechnology, data storage, and other applications. Enzymatic polynucleotide synthesis has emerged as an alternative to the long-standing nucleoside phosphoramidite method for synthesis of polynucleotides. Enzymatic polynucleotide synthesis is performed with a template-independent polymerase such as terminal deoxynucleotide transferase (TdT) rather than a series of chemical reactions. Enzymatic polynucleotide synthesis has advantages over the nucleoside phosphoramidite method because it is performed in an aqueous environment and does not use toxic organic chemicals. Enzymatic polynucleotide synthesis also has the potential to create longer polynucleotides than the nucleoside phosphoramidite method.

However, template-independent polymerases add nucleotides in an unregulated manner. These polymerases can add any available nucleotide and can create random sequences if provided with multiple types of nucleotides. If only a single species of nucleotide is present, the nucleotide may be added repeatedly creating variable-length homopolymers. Thus, it is challenging to precisely control the base-by-base sequence of polynucleotides created through enzymatic polynucleotide synthesis. In contrast, with the established nucleoside phosphoramidite method, each synthesis cycle reliably adds only a single, specific nucleotide.

Techniques for highly parallel and automated enzymatic-based methods are clearly desirable for many applications such as data storage. However, controlling template-independent polymerases brings unique challenges that are not present in chemical phosphoramidite synthesis. This disclosure is made with respect to these and other considerations.

SUMMARY

This disclosure provides methods and devices for solid-phase de novo enzymatic synthesis of polynucleotides. Spatially addressable control of polynucleotide extension on the surface of an array allows for parallel synthesis of multiple polynucleotides with different sequences. The spatial control is provided by selectively removing blocking groups that cap the 3' ends of polynucleotide strands attached to the array. Strand capping prevents a polymerase from adding nucleotides to the end of a polynucleotide. Once caps on the polynucleotide strands at a selected location are removed, the template-independent polymerase is able to add nucleotides to those strands. Polynucleotide strands that remain capped with 3' blocking groups are not extended. A single species of nucleotide is provided with the template-independent polymerase to control which base is incorporated. The template-independent polymerase and free nucleotides are removed through washing. Any polynucleotides with available 3'-OH groups are capped again by addition of 3' blocking groups.

This process is repeated multiple times to synthesize polynucleotides with any desired sequence. The selected location where the caps are removed and the selected nucleotide species may both be independently changed in subsequent rounds of polynucleotide extension. Upon completion of synthesis, the array is covered with many polynucleotide strands that have different, arbitrary sequences.

In one implementation, the 3' blocking groups are acyl groups added to the 3'-OH of polynucleotides attached to the array. Acylation may be performed by incubating the array with attached polynucleotides in a solution of acyl imidazole. Acyl imidazole may be dissolved in water at a concentration of about 1 M. The acyl imidazole solution may be adjusted to a pH of about 8 with sodium hydroxide, tris buffer, or another buffer. The acyl imidazole solution may be maintained in contact with the array for about one minute.

The acyl groups, or other 3' blocking groups, may be removed from the ends of the polynucleotides at the selected location by creation of a localized basic environment. The localized basic environment may be created by electrochemistry. An electrode, such as a microelectrode integrated into the array, may cause deacylation in proximity to the electrode by generating a negative voltage that removes the acyl groups and produces free 3'-OH groups. The negative voltage may be about −1.2 to −2.0V. The negative voltage may be applied for about 90 seconds. Prior to activation of the electrode, the array may be contacted with a deacylation solution that contains a buffer to carry negative charge generated at the electrode to the acyl groups. The deacylation solution may be buffered to about pH 7.4 with a potassium phosphate or similar buffer.

Localized basic environments that cause deacylation, or removal of another base-cleavable 3' blocking group, may be created by techniques other than electrochemistry. For example, small volumes of a base may be added to the selected location on the array by a fluid deposition instrument such as a chemical inkjet printer. Also, a photobase that is already present in solution may be excited by targeted exposure of the selected location on the array to a light source.

The use of 3' blocking groups other than base-cleavable groups is also contemplated. One alternative type of 3' blocking groups are acid-cleavable blocking groups. These 3' blocking groups are removed by creation of a localize acidic environment. Another alternative type of 3' blocking groups are photocleavable blocking groups. Photocleavable blocking groups are selectively removed by exposure to a light source. Either may be used in the same manner as base-cleavable blocking groups with modifications to the technique for removal of the blocking groups. Other blocking groups that can be removably attached to the 3'-OH of a polynucleotide include, but are not limited to, carbamates, carbonates, and ketals.

In an implementation, the nucleotides added to the 3' ends of the polynucleotide strands are unmodified nucleotides. Because template-independent polymerases perform unregulated synthesis, multiple nucleotides may be added to the end of each polynucleotide strand that does not have a 3' blocking group thereby creating homopolymers. The average length of the homopolymers can be regulated by controlling the length of incubation. Incubation with the template-independent polymerase and free nucleotides may be stopped by washing the array with a wash solution.

In an implementation, the nucleotides added to the 3' ends of the polynucleotide strands are 3'-OH modified nucleotides that include a 3' blocking group attached to each nucleotide. In this implementation, the template-independent polymerase is a modified polymerase that is capable of incorporating 3'-OH modified nucleotides. The presence of blocking groups on the free nucleotides limits addition to a single nucleotide during each round of synthesis. The 3-OH modified nucleotides may be acylated 3'-dNTPs.

Array-based synthesis of polynucleotides improves the scalability and throughput of previous enzymatic synthesis techniques that use beads in a test tube for solid-phase synthesis. All polynucleotides synthesized in the same test tube, plate well, or reaction chamber, are exposed to the same conditions and thus will have the same sequence of nucleotides. This requires a physically separate reaction environment for each unique polynucleotide sequence that is synthesized. However, array-based synthesis techniques in which 3' blocking groups can be removed from specific polynucleotides in a spatially-addressable manner makes it possible to synthesize multiple polynucleotides with different sequences on the same array. This design is more compact and requires less physical manipulation than a comparable system in which each unique polynucleotide sequence must be created in a different tube or well.

This disclosure also provides a device for de novo synthesis of polynucleotides using an array and a reaction reagent solution containing template-independent polymerase. This device includes reservoirs and fluid delivery pathways for adding the reaction reagent solution and selected species of nucleotides to the surface of the array. The device also includes an apparatus for spatially controlling removal of 3' blocking groups at a selected location on the array by any one of multiple techniques for addressably creating a localized basic environment. Control circuitry included in the device is configured to open the various fluid delivery pathways and to operate the apparatus for removal of the 3' blocking groups. The control circuitry may operate according to preprogrammed instructions that cause the device to synthesize multiple polynucleotides with different, predetermined sequences.

The apparatus for spatially controlling removal of 3' blocking groups may be implemented in a number of different ways. In an implementation, this apparatus is a microelectrode array with individually addressable electrodes and the generation of a negative voltage at individual electrodes removes the 3' blocking groups. In an implementation, this apparatus is a targeted fluid deposition instrument such as a chemical inkjet printer that is used to add small volumes of base to specific locations on the surface of the array. In an implementation, the apparatus is a light source capable of activating photobases that may be included in the reaction reagent solution. The light source is directed onto the selected location by a digital micromirror device (DMD), photomask, or the like thereby creating a localized basic environment at that location.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method (s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
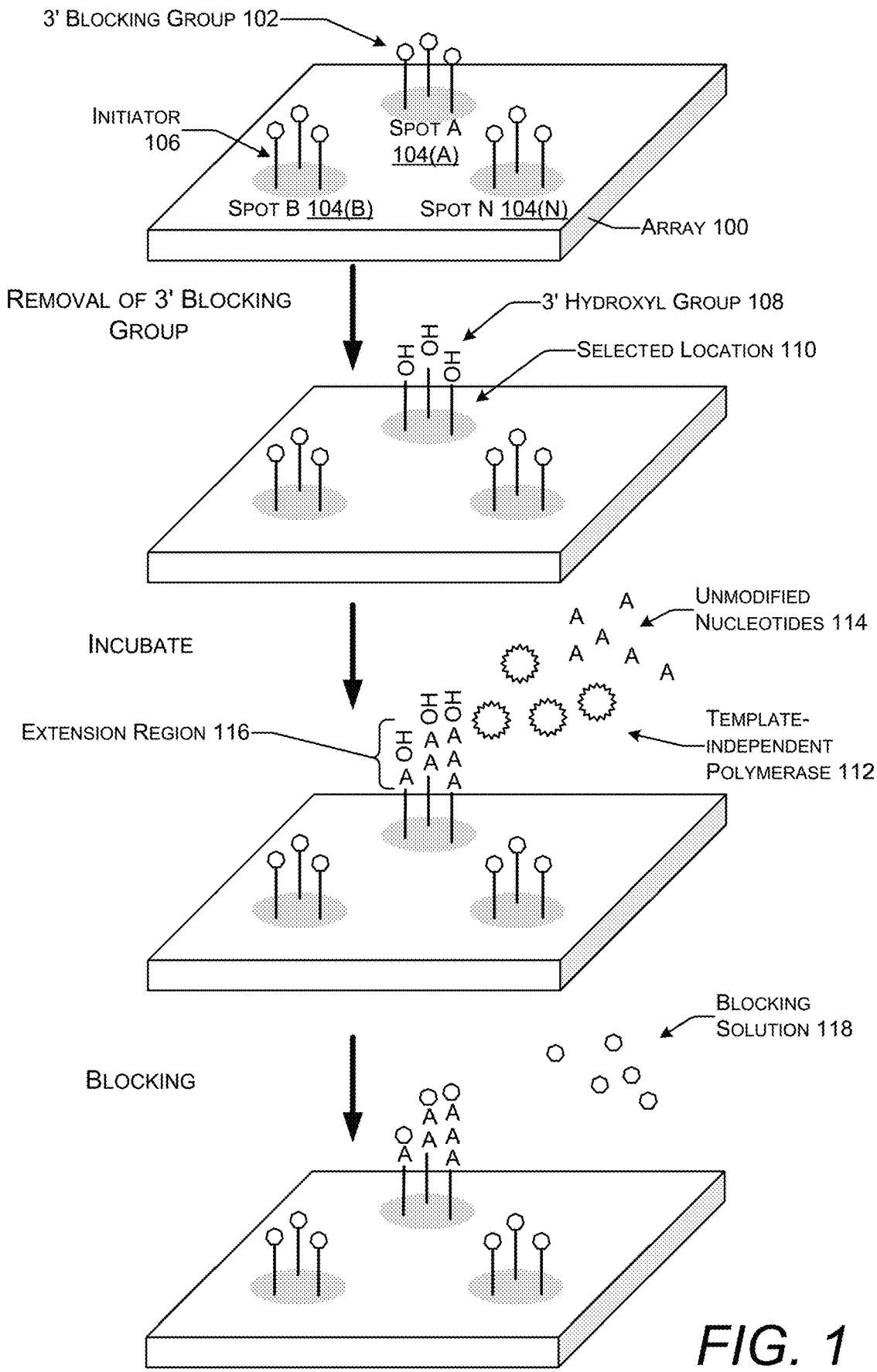
FIG. 1 shows solid-phase polynucleotide synthesis on an array using unmodified nucleotides in which the spatial location of polynucleotide extension is controlled by 3' blocking groups.

This disclosure provides techniques for solid-phase de novo enzymatic synthesis of polynucleotides with arbitrary sequences by controlling strand capping of polynucleotides. Spatially-selective removal of 3' blocking groups on some polynucleotides without removal from the remaining polynucleotides enables synthesis of a variety of polynucleotides on the same array. This provides a highly parallelized and efficient technique for creating a large number of polynucleotides each with specific and distinct sequences.

There are many uses for synthetic polynucleotides having specified sequences such as basic research, medicine, and nanoengineering (e.g., DNA origami). One relatively recent application for synthetic polynucleotides is digital data storage. Polynucleotides such as DNA may be used to store digital information by designing a sequence of nucleotide bases that encodes the zeros and ones of the digital information. There are various techniques and encoding schemes known to those of skill in the art for using nucleotide bases to represent digital information. See Lee Organick et al., *Random Access in Large-Scale DNA Data Storage,* 36:3 Nat. Biotech. 243 (2018) and Melpomeni Dimpoulou et al., *Storing Digital Data Into DNA: A Comparative Study of Quaternary Code Construction,* ICASSP Barcelona, Spain (2020). Advantages of using polynucleotides rather than another storage media for storing digital information include information density and longevity. The sequence of nucleotide bases is designed on a computer and then polynucleotides with those sequences are synthesized. The polynucleotides may be stored potentially for hundreds of years. Polynucleotides retrieved from storage are read by a polynucleotide sequencer and the base sequences are decoded to retrieve the digital information.

Most work with enzymatic polynucleotide synthesis does not consider techniques for efficient, parallel synthesis of polynucleotides with distinct sequences. For example, techniques that use beads as a solid substrate for synthesis create batches of polynucleotides with the same sequence. See, e.g., Sebastian Palluk et al., De novo *DNA synthesis using polymerase-nucleotide conjugates,* 36(7) Nature Biotechnology 645 (2018) and Henry H. Lee et al., *Terminator-free template-independent Enzymatic DNA Synthesis for Digital Information Storage,* 10:2383 Nat. Comm. (2019). Use of these techniques to create a large number of polynucleotides with different sequences for applications such as data storage would be impractical because of the large number of separate reaction chambers required.

These solid-phase enzymatic nucleotide synthesis techniques involve initiators attached to beads in a test tube or other discrete reaction chamber. The reaction chamber is flooded with an aqueous solution containing TdT and only one type of dNTP. Once coupling has taken place, the TdT and any free dNTPs are washed away. The beads are incubated in a second step with TdT and a different dNTP. The process continues creating DNA molecules with sequence specified by the order in which the different dNTPs are added. Depending on the control technique used, TdT may add a single nucleotide or an uncontrolled number of the same nucleotide during each cycle synthesis. This process does not scale well for applications that require high throughput synthesis of multiple polynucleotides with different sequences.

However, there are some techniques for enzymatic solid-phase synthesis that use spatial addressability to create polynucleotides with different sequences on a solid substrate. These techniques do so by regulating the availability of metal cofactors necessary for enzyme activity. One technique keeps the metal cofactors in an inactive state by caging with DMNP-EDTA and releases the metal cofactors at specific locations by exposure to patterned ultraviolet (UV) light. Diffusion of the metal cofactors is controlled by providing an excess of the caging molecules. The TdT and nucleotides are provided in a standard synthesis master mix. See Howon Lee et al., *Photon-directed Multiplexed Enzymatic DNA Synthesis for Molecular Digital Data Storage*, bioRxiv 2020.02.19.956888.

A different technique, also by the inventors of this application, controls the oxidation state of metal enzyme cofactors. The metal cofactors are changed from an oxidation state of +2 that complexes with the enzyme to a different oxidation state that does not. Template-independent polymerase is inactive unless metal cofactors with an oxidation state of +2 are available. Spatial control of the oxidation state is achieved by activation of electrodes on a microelectrode array, controlled addition of redox reagents, or other techniques. Diffusion of the metal cofactors in the +2 oxidation state is controlled by scavenger molecules that either change the oxidation state or sequester the metal cofactors. See U.S. patent application Ser. No. 16/543,433 filed on Aug. 16, 2019, with the title "Regulation of Polymerase Using Cofactor Oxidation States."

A third technique that considers synthesis on an array uses the enzyme apyrase which degrades nucleoside triphosphates into their TdT-inactive diphosphate and monophosphate precursors to regulate TdT activity. In this technique, apyrase limits polymerization by competing with TdT for nucleoside triphosphates. See Henry H. Lee et al. supra, and WO 2017/176541 A1.

In contrast to regulating polymerase activity by control of metal cofactor availability or degrading nucleotides, this disclosure provides techniques to control the location of nucleotide incorporation by spatially-selective removal of 3' blocking groups on polynucleotide strands attached to an array. In the techniques of this disclosure, active template-independent polymerase with all necessary metal cofactors and free nucleotides may be present across the entire surface of the array.

Polynucleotides, also referred to as oligonucleotides, include both DNA, RNA, and hybrids containing mixtures of DNA and RNA. Polynucleotides are polymers of nucleotides. DNA includes nucleotides with one of the four natural bases cytosine (C), guanine (G), adenine (A), or thymine (T) as well as unnatural bases, noncanonical bases, and/or modified bases. RNA includes nucleotides with one of the four natural bases cytosine, guanine, adenine, or uracil (U) as well as unnatural bases, noncanonical bases, and/or modified bases. Polynucleotides may also include chemical variants thereof, such as methylated, hydroxymethylated or glycosylated forms of the bases, and the like.

Nucleotides are nucleosides covalently linked to one or more phosphate groups and include both deoxyribonucleotides and ribonucleotides. Unmodified nucleotides, or natural nucleotides, refers to one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP). Natural nucleotides lack chain-terminating blocking groups.

Modified nucleotides have one or more changes to the sugar moiety or the base moiety that are not found in natural nucleotides. 3'-OH modified nucleotide as used herein refers to nucleotides with a cleavable 3' blocking group that once incorporated into a polynucleotide strand terminates further extension by preventing incorporation of additional nucleotides. Upon removal of the blocking group the 3'-OH group is restored leaving a nucleotide that (absent other separate modifications) is essentially identical to a natural nucleotide. A wide variety of 3'-OH modifed nucleotides are known to those of ordinary skill in the art. Some illustrative 3' blocking groups include azidomethyl groups, allyl groups, acyl groups, amino groups, and —$CH_2CN$. Examples of 3'-OH modifed nucleotides are described in WO 2003/048387; WO 2004/018497; WO 1996/023807; WO 2008/037568; WO 2016/034807; Ser. Nos. 10,059,929; 10,683,536; Hutter D., et al. *Nucleosides Nucleotides Nucleic Acids,* 2010, 29(11): 879-95; and Knapp et al., *Chem. Eur. J.,* 2011, 17:2903. Further examples of 3' blocking groups include 3'-O-amino, 3'-O-allyl, and a 3'-O-azidomethyl groups. 3' blocking groups may also include O-phenoxyacetyl; O-methoxyacetyl; O-acetyl; O-(p-toluene)-sulfonate; O-phosphate; O-nitrate; O-[4-methoxy]-tetrahydrothiopyranyl; O-tetrahydrothiopyranyl; O-[5-methyl]-tetra-hydrofuranyl; O-[2-methyl,4-methoxy]-tetrahydropyranyl; O-[5-methyl]-tetrahydropyranyl; and O-tetrahydrothiofuranyl. See U.S. Pat. No. 8,133,669 for a discussion of these blocking groups.

In one implementation, 3' OH modified nucleotides are modified with a 3' acyl group. The term "acyl group" as used herein refers to a chemical entity comprising the general formula R—C(═O)— where R represents any aliphatic, alicyclic, or aromatic group and C(═O) represents a carbonyl. An acyl group may be an acetyl group, a propionyl group, a butyryl group, an isobutyryl group, a valeryl group, a pivaloyl group, a hexanoyl group, or the like. An acetyl group is an acyl group where R is a methyl group.

As used herein, template-independent polymerase means a polymerase enzyme that catalyzes extension of polynucleotide substrate or primer strand with nucleotides in the absence of a polynucleotide template. Template-independent polymerases where the polynucleotide substrate or primer is DNA are known as template-independent DNA polymerases. Template-independent polymerases where the polynucleotide substrate or primer is RNA are known as template-independent RNA polymerases. Template-independent polymerases may accept a broad range of nucleotide polyphosphate substrates. Template-independent DNA polymerase are defined to include all enzymes with activity classified by the Enzyme commission number EC 2.7.7.31 (See, enzymeiExPASy: SIB Bioinformatics Resource Portal, EC 2.7.7.31).

In an implementation, the template-independent polymerase is a template-independent DNA polymerase such as terminal deoxynucleotidyl transferase (TdT) of the polX family of DNA polymerases. Further description of TdT is provided in Biochim Biophys Acta., May 2010; 1804(5): 1151-1166. TdT creates polynucleotide strands by catalyzing the addition of nucleotides to the 3' end of a DNA molecule in the absence of a template. The preferred substrate of TdT is a 3'-overhang, but it can also add nucleotides to blunt or recessed 3' ends.

TdT may be of mammalian origin, for example, from bovine or murine sources. In other implementations, TdT is from other non-mammalian species. In some embodiments, the TdT is a member of the archaeo-eukaryotic primase (AEP) superfamily. In other embodiments, the TdT is a PolpTN2 or a C-terminal truncated PolpTN2, a PriS, a nonhomologous end-joining archaeo-eukaryotic primase, a mammalian P016, or a eukaryotic PrimPol. All of these and other types of TdT are known to those of ordinary skill in the art and described in US 2019/6360013.

In an implementation, the template-independent polymerase is a template-independent RNA polymerase such as tRNA nucleotidyltransferase. This enzyme is described in Kozo Tomita and Seisuke Yamashita, *Molecular mechanisms of template-independent RNA polymerization by tRNA nucleotidyltransferases*, Frontiers in genetics, vol. 5 36, (2014).

TdT as used herein includes both the full-length wild-type enzyme, as well as modified enzymes that are truncated or internally modified. One example of modified TdT is provided in U.S. Pat. No. 10,059,929. An example of truncated TdT is provided in U.S. Pat. No. 7,494,797. Thus, TdT as used herein includes full-length wild-type, truncated, or otherwise modified TdT that can perform template-independent synthesis of polynucleotides. TdT as used herein does not encompass modifications that render an enzyme incapable of performing nucleotide polymerization.

TdT is a protein that evolved to rapidly catalyze the linkage of naturally occurring deoxynucleotide triphosphates (dNTPs). TdT adds nucleotides indiscriminately to the 3' hydroxyl group at the 3' end of single-stranded DNA. TdT performs unregulated synthesis adding any available dNTP. TdT uses an existing polynucleotide referred to as an "initiator" as the starting point for synthesis. Initiators as short as three nucleotides have been successfully used with TdT for enzymatic synthesis of DNA. Suitable initiator length ranges from three nucleotides to about 30 nucleotides or longer. Initiators may be single-stranded or double-stranded. Double-stranded initiators may have a 3' overhang or they may be blunt ended or they may have a 3' recessed end. During polymerization, the template-independent polymerase holds a DNA strand (which initially is only the initiator but grows as synthesis proceeds) and adds dNTPs in a 5'-3' direction. TdT activity is maximized at approximately 37° C. and performs enzymatic reactions in an aqueous environment.

Native TdT is a very efficient enzyme. It has been demonstrated that TdT can polymerize extremely long homopolydeoxynucleotides of 1000 to 10,000 nucleotides in length (see Hoard et al., *J. of Biol. Chem.*, 1969 244(19): 536373; F. J. Bollum, *The Enzymes*, Volume 10, New York: Academic Press; 1974. p. 141-71; Tjong et al., *Anal. Chem.* 2011, 83:5153-59. Optimum ranges of pH for enzyme activity are known to those of ordinary skill in the art and may be found in F. J. Bollum, supra. The optimum pH for TdT is about 6-8 pH.

Because template-independent polymerases perform unregulated synthesis, using this class of enzyme to create a polynucleotide with a pre-specified arbitrary sequence requires regulation and control of the polymerization activity. One technique to regulate template-independent polymerases activity is limiting the available nucleotides to only a single type of deoxynucleoside triphosphate (dNTP) or nucleoside triphosphate (NTP) (e.g., only deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP)). Thus, providing only one choice forces the polymerase to add that type of nucleotide.

However, this does not prevent template-independent polymerases from adding the nucleotide multiple times thereby creating homopolymers. Techniques for limiting homopolymer creation by TdT include using nucleotides with removable protecting groups that prevent addition of more than one nucleotide at a time. Examples of techniques that use blocking groups attached to nucleotides are described in U.S. Pat. Nos. 10,059,929 and 10,683,536. These techniques describe 3'-OH modified dNTPs free in solution but do not discuss adding blocking groups to polynucleotides attached to an array or spatially-addressable removal of 3' blocking groups.

In some implementations, the template-independent polymerase may be attached to a single nucleotide so that the enzyme itself functions as a blocking group. With this technique, TdT enzymes are each tethered to a single dNTP by a cleavable linker. See Sebastian Palluk et al., supra, WO 2017/223517, and Sebastian Barthel et al., *Enhancing Terminal Deoxynucleotidyl Transferase Activity on Substrates with 3' Terminal Structures for Enzymatic De Novo DNA Synthesis*, 11(102) Genes (2020). This technique also discusses modifications to individual nucleotides free in solution rather than capping strands attached to an array.

Detail of procedures and techniques not explicitly described or other processes disclosed in this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, $4^{th}$ ed. (2012).

FIG. 1 shows an illustrative representation of solid-phase synthesis on an array 100 in which the location of nucleotide addition is regulated by spatially-addressable removal of 3' blocking groups 102 from polynucleotides attached to the array 100. The array 100 provides a solid support for solid-phase synthesis of polynucleotides. Solid-phase synthesis is a method in which molecules are covalently bound on a solid support material and synthesized step-by-step in a single reaction vessel.

The array 100 may be made of any material that is capable of anchoring polynucleotides. The array 100 may be formed from a silicon chip, glass (e.g., controlled porous glass (CPG)), an insoluble polymer, or other material. The array 100 being a generally flat two-dimensional surface provides for addressable, site-specific manipulations at specified locations (e.g., represented in terms of x- and y-coordinates) on the surface of the array 100. The array 100 may be an electrochemically inert surface or it may include an array of individually addressable microelectrodes.

Examples of microelectrode arrays are provided in Bo Bi et al., *Building Addressable Libraries: The Use of "Safety-Catch" Linkers on Microelectrode Arrays*, 132 J. Am. Chem. Soc. 17,405 (2010); Bichlien H. Nguyen et al., *Microelectrode Arrays: A General Strategy for Using Oxidation Reactions To Site Selectively Modify Electrode Surfaces*, 30 Langmuir 2280 (2014); and U.S. patent application Ser. No. 16/435,363 filed on Jun. 7, 2019, with the title "Reversing Bias in Polymer Synthesis Electrode Array." One example of a microelectrode array and techniques for attaching polynucleotides to the surface of the array is provided in a Ryan D. Egeland & Edwin M. Southern, *Electrochemically Directed Synthesis of Oligonucleotides for DNA Microarray Fabrication*, 33(14) Nucleic Acids Res. e125 (2005).

The electrodes in a microelectrode array may be implemented with any known technology for creating microelectrodes such as complementary metal-oxide-semiconductor (CMOS) technology. CMOS may include metal-oxide-semiconductor field-effect transistors (MOSFETs) made through a triple-well process or by a silicon-on-insulator (SOI) process. A series of controllable gates/transistors implemented with CMOS circuits can be controlled to inject charge at any location on the surface of the microelectrode array. Each electrode in the microelectrode in the array may be independently addressed allowing the creation of arbitrary and variable voltage microenvironments across the surface of the microelectrode array.

High microelectrode density allows for fine-scale level control of the ionic environment at the surface of the microelectrode array. A microelectrode array may have a microelectrode density of approximately 1024 microelectrodes/cm$^2$, approximately 12,544 microelectrodes/cm$^2$, or a different density.

The array 100 may be covered with a plurality of spots 104(A), 104(B), . . . , 104(N) at which initiators 106 are attached. Each of the initiators 106 is a single- or double-stranded polynucleotide strand. If double-stranded, the initiators 106 may have a 3' overhang, they may be blunt ended, or they may have a 3' recessed end. The length of an initiator 106 may be about 3-30 nucleotides, about 15-25 nucleotides, or about 20 nucleotides. The initiators 106 are not shown to scale. Because they are lengthened through repeated rounds of nucleotide addition, the initiators 106 and the polynucleotides that are synthesized from an initiator may be referred to as growing polynucleotide strands.

Although only three spots 104(A), 104(B), 104(N) are shown in this illustrative representation many thousands or hundreds of thousands of spots may be present on a typical array 100. The size of a single spot 104 can be smaller than about 1 cm$^2$, smaller than about 1 mm$^2$, smaller than about 0.5 mm$^2$, smaller than about 100 μm$^2$, smaller than about 50 μm$^2$, smaller than about 1 μm$^2$, smaller than about 500 nm$^2$, or smaller than about 200 nm$^2$. Initiators 106 may also be present on the array 100 at locations other than the spots 104.

The initiators 106 may be attached to the array 100 using any known technique for anchoring single-stranded DNA or RNA to a solid support such as techniques used in conventional solid-phase synthesis of polynucleotides or used for creation of DNA microarrays. For example, the initiators 106 may be spotted onto the array 100 by use of a robot to "print" pre-designed nucleotide sequences using fine-pointed pins, needles, or ink-jet printing onto a chemical matrix surface using surface engineering. Other methods employ photo-activated chemistry and masking to synthesize the initiators 106 one nucleotide at a time on the solid surface of the array 100 with a series of repeated steps to build up the initiators 106 at designated locations. In some implementations, the surface of the array 100 may be functionalized and the initiators 106 may be attached to the functional groups rather than directly to the array 100.

All of the initiators 106 attached to the array 100 may have the same or approximately the same nucleotide sequence or one or more of the initiators 106 may have different sequences from the others. The sequence of any one or more of the initiators 106 may be a random sequence of nucleotides. The initiators 106 may also be constructed with non-random sequences such as, for example, sequences that are cleaved by a specific restriction endonuclease. Cleavage of the initiators 106 is one way to release completed polynucleotides from the surface of the array 100. The sequences of the initiators 106 may also be designed or used as primer binding sites for subsequent amplification (e.g., polymerase chain reaction (PCR) amplification) of fully synthesized polynucleotides.

Each spot 104 on the array 100 may contain many tens or hundreds of initiators 106 although for simplicity only three initiators 106 are shown on each spot 104 in this illustrative representation. Each initiator 106 attached to a single spot 104 is subject to the same spatially addressable control. Stated differently, any spatially addressable removal of 3' blocking groups 102 is performed at the resolution of individual spots 104. However, the polynucleotides synthesized on the same spot 104 do not necessarily have identical nucleotide sequences because of the formation of variable length homopolymers.

The 3' blocking groups 102 are removed from a selected location on the array 100 that includes one or more spots 104. The 3' blocking groups 102 are initially attached to the 3' ends of initiators 106 on the surface of the array 100. The 3' blocking groups 102 may be added to the ends of the initiators 106 by incubating an array 100 covered with un-capped initiators 106 is a blocking solution. A blocking solution adds 3' blocking groups 102 to the 3' ends of the initiators 106. In one implementation, the blocking solution is a solution of acyl imidazole that adds acyl groups to the 3' ends of the initiators 106. Other techniques may also be used to add 3' blocking groups 102 to the initiators 106. For example, the initiators may be synthesized in situ on the surface of the array 100 with a final nucleotide added at the 3' end that includes a 3' blocking group 102. Synthesis of the initiators 104 on the array 100 may be performed by non-enzymatic techniques such as phosphoramidite synthesis.

The 3' blocking groups 102 are selectively removed from some but not all locations on the array 100. This creates an array 100 that has some initiators 106 with 3'-OH groups 108 and others that remain capped with a 3' blocking group 102. In this illustration, the 3' blocking groups 102 are removed from spot 104(A). The areas of the array 100, or the spots 104 on the area, from which 3' blocking groups 102 are removed is referred to as a selected location 110.

The selected location 110 may be any one or more locations that are contiguous or separate on the surface of the array 100. The selected location 110 may be a single spot 104, a group of spots located adjacent to each other, or multiple disparate spots spread across the surface of the array 100. The resolution or minimum size of the selected location 110 may be a single spot 104. The spots 104 may be spaced apart from each other creating a buffer zone that prevents 3' blocking group 102 removal that extends beyond the edge of one spot 104(A) from removing 3' blocking groups 102 at an adjacent spot 104(B).

A variety of different techniques may be used to remove 3' blocking groups 102 depending on the type of blocking group. In some implementations, the 3' blocking groups 102 are removed by an increase in pH that creates a localized basic environment. A localized basic environment may be created in an aqueous solution by a negative electrode voltage. Addition of a base can also create a localized basic environment. Photobases may also be used to create a localized basic environment upon exposure to a light source of a suitable wavelength.

Electrodes, such as a microelectrode array, may be used to change the pH of an aqueous solution electrochemically over a wide range. The maximum concentration limits of base and acid that can be produced in a given water sample limit the range of pH changes. These limits are determined by the kinds and concentrations of all elements dissolved in the water. It is possible, using electricity, to produce water with any content of base or acid within these limits. Electrochemical pH control is based on electrical decomposition of water in an electrolytic cell divided by an ion-exchange membrane or diaphragm into anode and cathode compartments. The minimum (theoretical) voltage necessary to decompose water is 1.23 V at 25° C. Actual decomposition voltage is higher because of the irreversible nature of electrodes. A visible evolution of gases ($O_2$ and $H_2$) commences at 1.7 V. See Albert Regner, *Electrochemical processes in chemical industries*. Artia, Prague: 198-212 (1957). Usually either the anodic or the cathodic reaction is used for pH control, while the complementary reaction may be undesired in some practical applications.

Acyl groups are one example of 3' blocking groups 102 that can be removed by a localized basic environment. In some implementations, the acyl groups comprise acetyl groups. Acyl groups may be removed by a voltage of about −1.4 to −2.0 V. For example, the voltage may be about −1.6 V. Prior to application of the voltage at the selected location 110, the array 100 may be contacted with a deblocking solution that contains electrolytes. One example of a deblocking solution is a solution of a potassium phosphate buffer.

In other implementations, a decrease in pH that creates a localized acidic environment may be used to remove 3' blocking groups 102 at a selected location 110. The localized acid environment cleaves acid-cleavable blocking groups. Acid-cleavable blocking groups such as a ethyl vinyl ether acetal or tert-butylcarbonate may be attached to the 3' end of a nucleotide. These linkers are designed to remain stable at neutral pH but undergo hydrolysis in an acidic environment.

In yet other implementation, the 3' blocking group 102 may be photocleavable. A photocleavable blocking group is removed by exposure to a light source of a specific wavelength. Exposure to light may cause the 3' blocking group 102 to release from the end of an initiator 106 without any appreciable change in pH. There are a large number of known types of photocleavable chemical motifs that can be used to form photocleavable blocking groups. For example, one suitable photocleavable blocking group is alpha-methyl-2-nitro-benzylcarbonate. Additional examples of photocleavable chemical motifs are provided in Thangaiah Subramanian et al., *Protein Farnesyltransferase Catalyzed Isoprenoid Transfer To Peptide Depends On Lipid Size and Shape, not Hydrophobicity*, 9(17) Chembiochem 2872 (2008) and Ken-ichiro Hayashi et al., *Caged gene-inducer spatially and temporally controls gene expression and plant development in transgenic Arabidopsis plant*, 16 Biootganic & Medicinal Chem. Let. 2470 (2006).

The availability of 3'-OH groups 108 makes it possible for nucleotides to be incorporated onto the ends of the initiators 106 at spot A 104(A) without adding nucleotides to initiators 106 at spot B 104(B) or spot N 104(N). Each added nucleotide extends the initiator 106 which becomes a growing polynucleotide strand. In a synthesis cycle, the array 100 is incubated with a reaction reagent solution that contains template-independent polymerase 112. The reaction reagent solution is an aqueous solution that includes the template-independent polymerase 112 and may also include buffers, salts, electrolytes, and the like. For example, the aqueous solution may include TdT buffer and a $CoCl_2$ solution to supply metal cofactors for the polymerase.

A single species of unmodified nucleotide 114 (i.e., dATP, dGTP, dCTP, dTTP, ATP, GTP, CTP, or UTP) is also provided. Addition of only a single species of unmodified nucleotide 114 limits the template-independent polymerase 112 from randomly adding any nucleotide species. The array 100 may be incubated with the template-independent polymerase 112 and the single species of unmodified nucleotide 114 for a reaction time which may be about 10, 20, 30, 40, 50 seconds, 1 minute, or 2 minutes.

The unmodified nucleotide 114 in this illustrative representation includes the base adenine (A) such as dATP or ATP. The unmodified nucleotides 114 may be provided as free nucleotides in solution. After the template-independent polymerase 112 has had time to react with free nucleotides in solution a wash step may be used to remove the template-independent polymerase 112 and free nucleotides stopping extension of the initiators 106. Depending on the length of time the template-independent polymerase 112 is in contact with the initiators 106, multiple unmodified nucleotides may be added creating a homopolymer. Thus, the polynucleotide synthesis techniques of this disclosure may create block polymers in which the base-by-base sequence of polynucleotides on the same spot 104 is not always identical. However, the order of nucleotide blocks will be the same.

For example, a first cycle of synthesis may add from one to three adenine nucleotides to the 3' end of the initiators 106 at spot A 102(A). Additional nucleotides added during a single cycle of synthesis are referred to as extension region 116. This variation arises from the ability of template-independent polymerase 112 to perform unregulated polymerization. Under a given set of reaction conditions the number of nucleotides added in an extension region 116 will vary with a distribution concentrated around a mean extension length. The reaction conditions include temperature, time, and the concentrations of the nucleotide, and concentration of the template-independent polymerase. The extension length may be tuned by adjusting the reaction time.

Thus, unless context indicates otherwise, "extension length" refers to the average extension length for a given set of reaction conditions. This variation in extension length for individual ones of the polynucleotides is the reason why a population of polynucleotides at the same spot 104 may have different sequences. Due to the presence of homopolymers it may not be possible to synthesize polynucleotides with specific base-by-base sequences using unmodified nucleotides 114.

However, polynucleotides that have a specified order of nucleotide bases even if the precise number of nucleotides is not controllable have uses in applications such as digital data storage. Data may be included in nucleotide transitions rather than by the absolute sequence. Techniques for encoding digital data using nucleotide transitions in polynucleotides with homopolymers are discussed in Henry H. Lee et al. supra, WO 2017/176541 A1, and U.S. patent application Ser. Nos. 16/543,433 and 16/563,797.

The unmodified nucleotides 114 once incorporated onto the ends of the initiators 106 have 3' OH groups that are available for further extension during a subsequent cycle of synthesis. However, during subsequent cycles of synthesis the selected location 110 may be changed. Thus, to prevent addition of more nucleotides at the same location such as spot A 104(A), the entire array 100 may be incubated with a blocking solution 118. The blocking solution 118 adds 3' blocking groups where there are free 3' OH groups on the end of a polynucleotide. One example of a blocking solution 118 is an acylation solution of acyl imidazole that adds acyl groups where there are free 3' OH groups. The array 100 may be incubated with the blocking solution 118 for a period of time such as from about 30 seconds to about 30 minutes. This "resets" the array 100 so that all of the polynucleotide strands attached to the array 100 are capped with 3' blocking groups 102. In subsequent synthesis cycles, the 3' blocking groups 102 are again removed at a selected location 110 and polynucleotide extension can occur potentially at a different location on the array 100.

Figure 2:
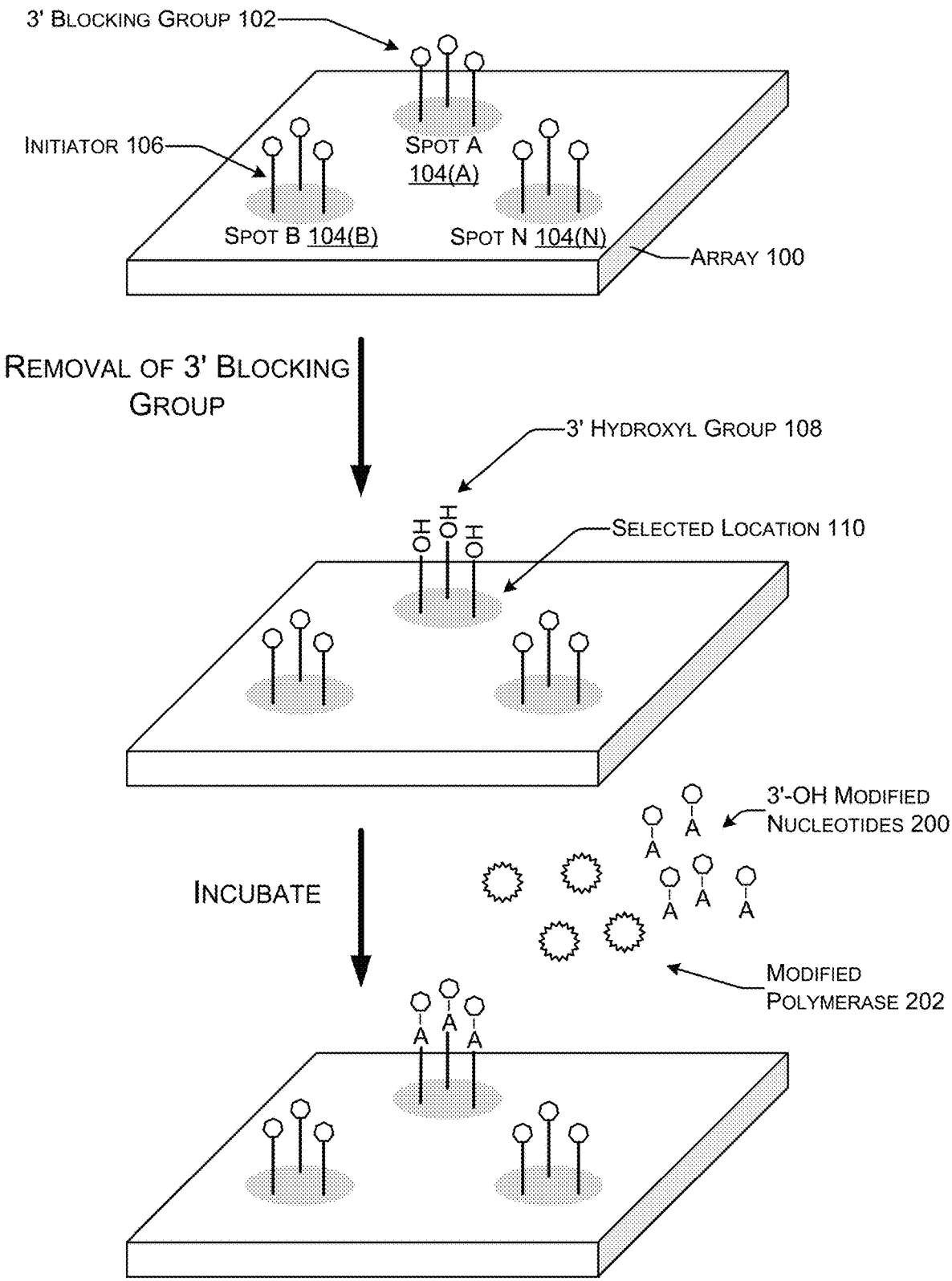
FIG. 2 shows solid-phase polynucleotide synthesis on an array using 3' OH modified nucleotides in which the spatial location of polynucleotide extension is controlled by 3' blocking groups.

FIG. 2 shows a variation of the solid-phase synthesis technique illustrated in FIG. 1 using 3'-OH modified nucleotides 200 instead of unmodified nucleotides 114. The 3'-OH modified nucleotides 200 may be any type of nucleotide that includes a cleavable 3'-O-blocking group. In one implementation, the 3'-OH modified nucleotides 200 comprise acetylated 3'-dNTPs or acetylated 3'-NTPs. Techniques for creating modified nucleotides that include a 3' blocking groups are known to those of skill in the art. Illustrative 3' blocking groups are described in U.S. patent application Ser. No. 16/886,638 filed on May 28, 2020, with the title "De novo polynucleotide synthesis with substrate-bound polymerase." Water-based techniques for acylation of nucleotides are discussed in Christian Fernández-Garcia and Matthew W. Powner, *Selective Acylation of Nucleosides, Nucleotides, and Glycerol-3-phosphocholine in Water,* 28(01) Synlett 78 (2017).

In an implementation, the 3'-OH modified nucleotides 200 may be nucleotides tethered to a TdT. Thus, the enzyme acts as its own blocking group. The tether can be cleaved releasing the enzyme. The nucleotide added to the end of a growing polynucleotide strand would then be capped with 3' blocking group 102 such as an acyl group. Techniques for achieving single base addition with nucleotides tethered to TdT are described in U.S. Pat. No. 10,059,929.

The presence of a blocking group on the free nucleotides in solution limits the template-independent polymerase 112 to addition of only a single nucleotide during each cycle of synthesis. Thus, by use of 3'-OH modified nucleotides 200 with protecting groups, the synthesis techniques of this disclosure can be used to create polynucleotides with specific base-by-base sequences. Because incorporation of a nucleotide adds a 3' blocking group 102, there is no need for a blocking solution 118 to cap 3'-OH groups 108 as illustrated in FIG. 1. The blocking groups on the 3'-OH modified nucleotides 200 may be the same as the 3' blocking groups 102 attached to the initiators 102 (e.g., both acyl groups). Alternatively, the blocking groups on the 3'-OH modified nucleotides 200 may be different. In some implementations, the two different types of blocking groups may both be removed by the same conditions such as the same localized basic environment.

The array 100 is incubated with a reaction regent solution containing 3'-OH modified nucleotides 200 and a modified polymerase 202. A modified polymerase 202 as used herein is a template-independent polymerase 112 modified to incorporate 3'-OH modified nucleotides 200. In one implementation, the modified polymerase 202 may be a polymerase tethered to a nucleotide as described in U.S. Pat. No. 10,059,929. A modified polymerase 202 may also be created by directed evolution to incorporate a specific type of 3'-OH modified nucleotide 200 such as acylated nucleotides. Directed evolution has been used successfully to create a thermostable TdT variant as described in Jasmine Puay Suan Chua et al., *Evolving a Thermostable Terminal Deoxynucleotidyl Transferase,* 9(7) ACS Synthetic Biology 1725 (2020). Techniques for creating modified TdT that can incorporate 3' blocked nucleotides are described in U.S. Pat. Pub. Nos. 2020/0002690 and 2018/0023108 and U.S. Pat. No. 10,059,929.

Illustrative Process

Figure 3:
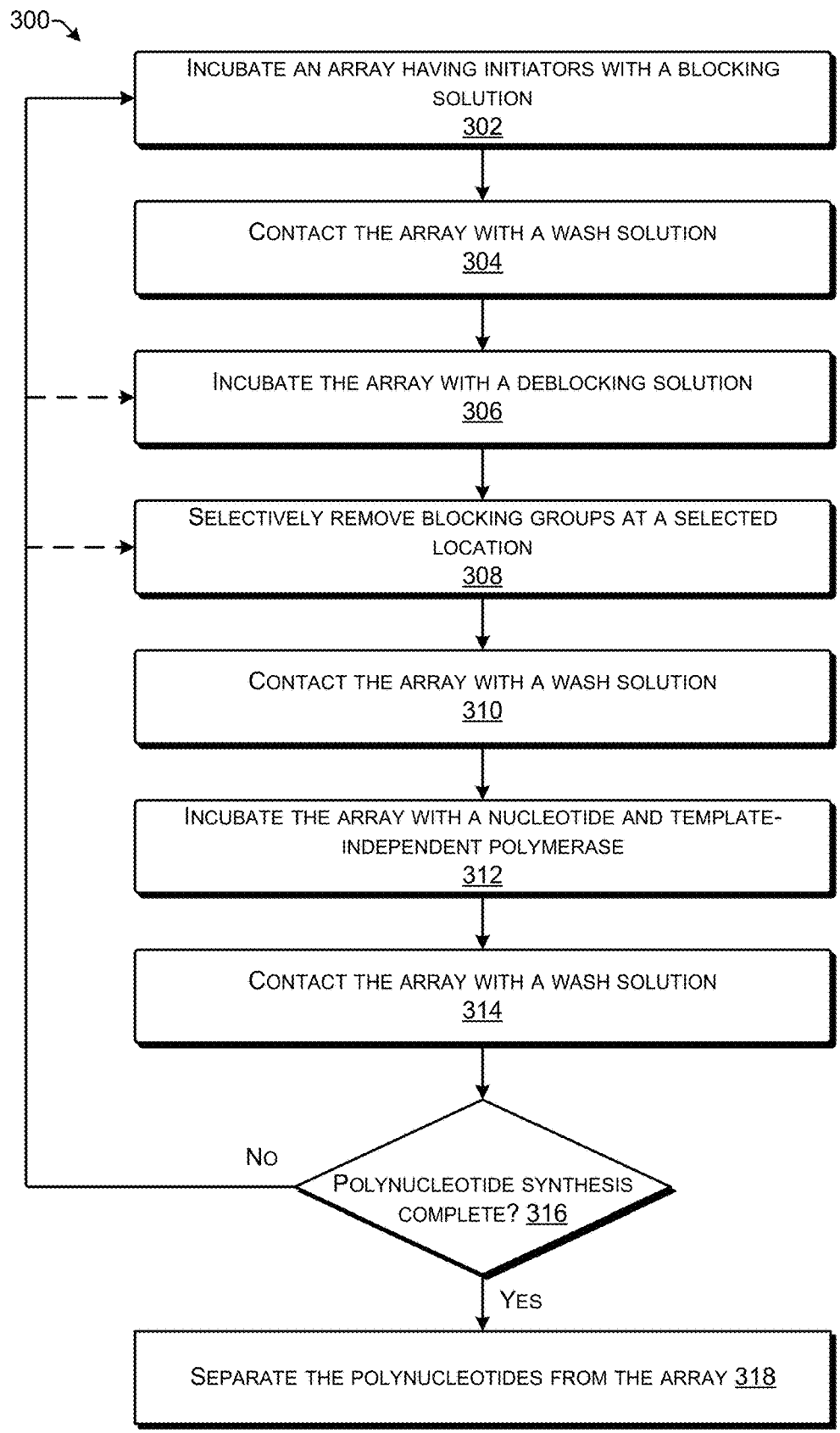
FIG. 3 is a flow diagram showing an illustrative process for solid-phase polynucleotide synthesis using 3' blocking groups to provide spatial control of polynucleotide extension.

FIG. 3 shows process 300 for enzymatic synthesis of polynucleotides using 3' blocking groups to provide spatial control of polynucleotide extension. This process 300 may be implemented, for example, using any of the processes, techniques, or reactions, shown in FIG. 1 or 2 or the device shown in FIG. 4.

At operation 302, an array having a plurality of initiators attached thereto is incubated with a blocking solution that adds 3' blocking groups to the 3'-OH groups on the initiators. The incubation is performed for a time sufficient to add 3' blocking groups onto all or substantially all of the 3'-OH groups at the ends of the initiators. Incubation may be performed, for example, for about 30 seconds to about 30 minutes. The blocking solution may be an aqueous solution prepared with, for example, deionized (DI) water. The blocking solution may include an organic component or may be an entirely organic solution with no water. The organic component of the blocking solution may be, but is not limited to, any one or more of acetonitrile, ethanol, tetrahydrofuran (THF), dimethyl sulfoxide (DMSO), and glycerol. Any number of suitable buffers known to those of ordinary skill in the art may be used in the blocking solution. For example, the blocking solution may be buffered with sodium hydroxide or tris buffer. The blocking solution may be adjusted to a pH from about 7-9 such as a pH of about 8.

The blocking solution may be an acylation solution that adds acyl groups such as acetyl groups to the 3'-OH groups on the initiators. Thus, attaching 3' blocking groups to the plurality of initiators may be accomplished by acylating the 3'-OH groups on the plurality of initiators. One technique for acylating the 3'-OH groups is incubation of the array with an acylation solution containing acyl imidazole and a buffer. The acylation solution may be used with a wide range of acyl imidazole concentrations. For example, acyl imidazole may be present in the acylation solution at concentrations from about 10 mM up to the limits of solubility. In an illustrative implementation, acyl imidazole is present at a concentration of about 1 M. The acylation solution and techniques for acylating may be adapted from in Christian Fernández-Garcia and Matthew W. Powner, supra.

The array may be made out of silicon dioxide, glass, an insoluble polymer, or other material. In an implementation, the array is a microelectrode array. A plurality of initiators are attached to the surface of the array. The array may be covered with many thousands or millions of separate initiators. The initiators are single- or double-stranded nucleotides with a length of between about 3-30 bases. Each of the initiators may be identical having the same length and nucleotide sequence. However, there may also be variation among the initiators in terms of length as well as sequence. In some implementations, the sequences of the initiators may include a cut site for restriction enzymes or other nucleases to cleave the polynucleotides from the surface of the array. In some implementation, the initiators may serve as primer binding sites for subsequent amplification of the polynucleotides synthesized on the array.

A template-independent polymerase uses the initiators as a starting point for addition of additional nucleotides to the 3' terminal nucleotide at the end of each initiator. The initiators may be attached to the array by any known or later developed technique for anchoring single-stranded DNA or RNA to a solid support. Example techniques include those used in conventional solid-phase synthesis of DNA and used for creation of DNA microarrays.

At operation 304, the array is optionally contacted with a wash solution. The wash solution displaces the blocking solution from the surface of the array. The wash solution may be water such as DI water. The wash solution may be an aqueous solution that contains at least one of a salt or a buffer. The wash solution may also include an organic component or may be an entirely organic solution with no water. The buffer may be any one of a number of aqueous buffers known to those of ordinary skill in the art that are compatible with polymerases and single-stranded nucleotides such as phosphate-buffered saline (PBS) or tris-buffered saline (TBS). In some implementations, the wash solution may contain a small quantity of surfactant such as sodium dodecyl sulfate (e.g., 0.1% SDS solution). The array may be dried under a stream of compressed air or nitrogen following the wash.

At operation 306, the array is optionally incubated with a deblocking solution. The deblocking solution may be an electrolyte solution. Covering the array with an electrolyte solution allows current from electrodes to change the pH of the solution. The buffer may be, for example, a potassium phosphate buffer. A concentration of the buffer may be about 50 mM and the pH of the buffer may be between about 4-10 for example pH 7.4. If the 3' OH blocking groups are acyl groups, the deblocking solution may be referred to as a deacylation solution.

In implementations that do not use electrode potential to remove the 3' blocking groups this step may be omitted. Alternatively, the deblocking solution may not necessarily contain electrolytes but may contain photobases to generate base upon exposure to a light source.

At operation 308, the 3' blocking groups are selectively removed from the initiators at a selected location on the array. Spatially addressable removal of the 3' blocking groups at the select location removes those 3' blocking groups without removing 3' blocking groups at other locations on the array. This creates a patterned array on which the initiators or polynucleotide strands at the selected location have 3'-OH groups that can be extended by addition of nucleotides while initiators or polynucleotide strands on the remainder of the array are capped and cannot be extended.

The selected location may be any one or more locations that are contiguous or separate on the surface of the array. The selected location on the array may be one or more spots that each contain multiple individual initiators such as the spots 104 illustrated in FIGS. 1 and 2. The selected location may be a single spot, a group of spots located adjacent to each other, or multiple disparate spots spread across the surface of the array in any pattern. The selected location may be changed one or more times during the synthesis of polynucleotides on the array.

The 3' blocking groups may be removed from the ends of initiators or polynucleotides attached to the array at the selected location by any number of different techniques. In one implementation, the 3' blocking groups are base-cleavable and selective removal comprises creation of a localized basic environment at the selected location. For example, the 3' blocking groups may be acyl groups and they may be selectively removed by deacylating the initiators at the selected location through creation of a localized basic environment. In one implementation, the 3' blocking groups are acid-cleavable and selective removal comprises creation of a localized acid environment at the selected location. In one implementation, the 3' blocking groups are photocleavable and selectively removing the 3' blocking groups comprises exposing the selected location to a light source.

In the implementation in which the 3' blocking groups are removed by creation of a localized basic environment, any one of multiple different techniques may be used to create the localized basic environment. The localized basic environment may be created in a spatially addressable way by voltage generated at an electrode on a microelectrode array, a base applied by a targeted fluid deposition instrument, or a photobase in solution activated by exposure to a light source. Examples of photobase generators include carbamates, O-acyloximes, and ammonium salts. See e.g., Kanji Sugiyama and Masamitsu Shirai, *Photobase generators: Recent progress in application trend in polymer systems*, 34(2) Progress in Polymer Sci. 194 (2009).

In one implementation, the localized basic environment is created by use of electrodes such as a microelectrode array. One or more electrodes at the selected location may be activated to generate a voltage of about −1.4 V to about −2.0 V between the working and active electrodes. In one implementation, the voltage is about −1.6 V. Activation of the electrodes occurs when the array is in contact with the deblocking solution. The electrodes may be activated for about 60-120 seconds such as about 90 seconds. Thus, incubation with the deblocking solution at operation 306 occurs for slightly longer than the period of electrode activation.

In a second implementation, the localized basic environment is created by a base applied to the selected location on the array. The base may be any base that increases the pH without inhibiting activity of the template-independent polymerase. Examples of bases include sodium hydroxide, potassium hydroxide, magnesium hydroxide, lithium hydroxide, ammonium hydroxide, and calcium hydroxide. The solution covering the array when the base is added may be the wash solution added at operation 304. The base may be applied to the selected location by a targeted fluid deposition instrument that precisely deposits small volumes of liquid at specified locations. The volume and concentration of the base are selected such that the pH increases by an amount sufficient to remove the 3' blocking groups at the selected location without affecting 3' blocking groups outside of the selected location. For example, to remove acyl groups the pH may be increased to about 10, about 11, about 12, or about 13.

In a third implementation, photobases are exposed to a light source to create a localized basic environment. A light source of an appropriate wavelength to activate the photobases is directed on to the selected location by optoelectronics such as a photomask or DMD. In an implementation, the deblocking solution provided at operation 306 or the wash solution provided at 304 may include the photobases. Thus, photobases may be in contact with the entire surface of the array but are only activated on the locations exposed to a light source of the appropriate wavelength.

Photobases or photobase generators (PBGs) are molecules that convert light to proton transfer drive. "Photobase," as used herein, describes a compound which liberates a base upon exposure to a light source. Photobases are molecules that become more basic upon light excitation and include nitrogen-containing aromatic compounds such as quinolines and acridines. Some curcumins, xanthones, and Schiff bases have also been reported to be photobasic. Some examples of photobases include 2-nitrobenzyl cyclohexanecarbamate and triphenylsulfonium hydroxide. Examples of suitable photobases include tetraphenylborate salt of bicyclic guanidine base, 1,5,7-triaza-bicyclo[4.4.0]dec-5-ene (TBD) (Cheng B. Cao, et al., *Photo-induced crosslinking of water-soluble polymers with a new photobase generator,* 51(18) Polymer, 4058 (2010) and WPBG-266 which is water-soluble and available from FujiFilm Wako Pure Chemical Corporation.

At operation 310, the array is contacted with a wash solution. This wash solution may be the same or different than the wash solution used at operation 304. For example, the wash solution may be water alone or water combined with a small quantity of surfactant such as sodium dodecyl sulfate (e.g., 1% SDS solution). The water may be DI water. The wash solution displaces the solution used to remove the blocking groups. This may be the deblocking solution added at operation 306. The array may be dried under a stream of compressed air or nitrogen following the wash.

At operation 312, the array is incubated with a single species of nucleotide and template-independent polymerase. In some implementations, the template-independent polymerase is TdT. The template-independent polymerase may be provided in a reaction reagent solution. The reaction reagent solution is an aqueous solution that includes the template-independent polymerase and may also include buffers, salts, electrolytes, and the like. The reaction reagent solution may be delivered to a reaction chamber that contains the array. The reaction reagent solution may be added to the reaction chamber by a manual technique such as pipetting. The reaction reagent solution may be added to the reaction chamber by an automated or mechanized system such as via a fluid delivery pathway.

In one implementation, only unmodified nucleotides are incubated with the template-independent polymerase. For example, the single species nucleotide may be one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP).

To control the length of homopolymers created by the template-independent polymerase, the unmodified nucleotides may be incubated with the template-independent polymerase for a reaction time. The reaction time may be a predetermined duration. The duration of the reaction time affects the extension length. The reaction time may be about 10, 20, 30, 40, 50 seconds, 1 minute, or 2 minutes. TdT is known to incorporate different species of nucleotides at different rates and the rate of incorporation can also vary depending on the enzyme cofactor. Thus, there may be a separate reaction time for one or more of the species of nucleotides both as the final nucleotide at the 3' end of a polynucleotide strand and as the free nucleotide in solution that will be added. Thus, the reaction time may be varied based on the final nucleotide at the end of a polynucleotide strand and the next nucleotide to be added. Also, the reaction time may be based on the metal ion used as the enzyme cofactor.

In one implementation, the template-independent polymerase is incubated with 3'-OH modified nucleotides. For example, the 3'-OH modified nucleotides may be 3'-O-acetyl modified nucleotides. Alternatively, the 3'-OH modified nucleotides may be nucleotides each individually tethered to a template-independent polymerase as described in U.S. Pat. No. 10,059,929. If 3'-OH modified nucleotides are used, the template-independent polymerase may be a modified polymerase capable of incorporating 3'-OH modified nucleotides. The reaction time may be the same for every cycle of synthesis when using 3'-OH modified nucleotides because variable-length homopolymers will not be formed.

At operation 314, the array is contacted with a wash solution. This wash solution may be the same or different than the wash solutions provided at operation 304 and operation 310. The wash solution may be flowed across the entire array displacing the polymerase and any free nucleotides thereby stopping further extension of the growing polynucleotide strands. Thus, the timing of this wash step may be used to control the reaction time. The length of time until activity of the template-independent polymerase is stopped (e.g., by this wash step) may define the reaction time. The reaction time may also be limited by other techniques besides a wash step such as heating the template-independent polymerase to a temperature at which it loses activity.

Washing between separate cycles of synthesis also prevents contamination of free nucleotides from a previous cycle. The wash solution may be water such as DI water. The wash solution may be an aqueous solution that contains at least one of a salt or a buffer. The buffer may be any one of a number of aqueous buffers known to those of ordinary skill in the art that are compatible with polymerases and single-stranded nucleotides such as PBS or TBS. The wash solution may also include a denaturing agent such as a surfactant (e.g., 1% sodium dodecyl sulfate) or a protease (e.g., Proteinase K) to inactivate enzymes on the array.

At operation 316, it is determined if polynucleotide synthesis is complete. If all nucleotides needed to create specified sequences of the polynucleotides being synthesized on the array have been added to the initiators, then polynucleotides synthesis is complete. If complete, process 300 proceeds along the "yes" path to operation 318.

If, however, polynucleotide synthesis is not complete, process 300 proceeds along "no" path and may return to operation 302, operation 306, or operation 308.

If, at operation 312, the nucleotide is an unmodified nucleotide the polynucleotide strands at the selected location will have 3'-OH groups at their 3' ends. Unless capped, these 3'-OH groups will incorporate nucleotides during the next cycle of synthesis. To prevent this, the array is again incubated with a blocking solution. Once 3' blocking groups have been placed on all the initiators and polynucleotide strands attached to the array, process 300 may proceed to again selectively remove blocking groups at the selected location for the next cycle of synthesis. The selected location may, but does not necessarily, change during every cycle of synthesis.

If, at operation 312, the nucleotide is a 3'-OH modified nucleotide incorporation of the nucleotide during incubation with the template-independent polymerase at operation 312 adds blocking groups to the ends of the growing polynucleotide strands. Thus, there is no need to return to operation 302 and attach 3' blocking groups. Accordingly, process 300 may return to operation 306 and incubate the array with a deblocking solution in advance of selectively removing blocking groups at the selected location for the next cycle of synthesis.

In an alternate process that uses electrochemistry to create a localized basic environment, the 3' blocking groups may be removed by application of electrode voltage to the solution that is used to place the 3' blocking groups on the ends of the initiators. For example, the array may be incubated in an acylation solution at operation 302 and then process 300 may proceed directly to operation 308 where a voltage is generated by electrodes at the selected location. This alternate process omits operation 304 and operation 306. The voltage used to remove the acyl groups also destroys acyl imidazole at the selected location. Thus, the 3' blocking groups will not immediately reform.

Once the current is stopped acyl imidazole at other locations on the surface of the array could potentially diffuse to the selected location and reattach 3' blocking groups. However, selective removal of the blocking groups by activating electrodes at operation 308 may be followed shortly by the wash step at operation 310. The kinetics of diffusion and acylation are much slower than the time needed to contact the array with a wash solution. Thus, the deacylation or other selective removal of blocking groups is confined to the selected location.

If this alternative process is performed with unmodified nucleotides, process 300 proceeds from operation 316 to operation 302 and then to operation 308. If this alternative process is performed with modified nucleotides the addition of blocking groups at operation 302 is unnecessary and process 300 may return to operation 308 until polynucleotide synthesis is complete. This shorter cycle includes site-specific removal of acyl groups or other blocking groups by generating a negative voltage at an electrode at operation 308 then incubation of the array with a modified nucleotide and a modified template-independent polymerase at operation 312 each followed by respective wash steps.

In all of the paths that process 300 may follow, the array is again incubated with a selected species of nucleotide and template-independent polymerase. In a subsequent synthesis cycle the selected location and the species of nucleotide may both be independently changed. Process 300 may be repeated over many cycles such that both the selected location and the selected species of nucleotide are changed at least once. This allows for the parallel synthesis of multiple polynucleotides each with a different sequence on the surface of a single array.

At operation 318, the polynucleotides are separated from the array. If the polynucleotides are attached to the array by linkers, cleavage of the linkers may release the polynucleotides. The initiators used to start growth of polynucleotides on the array may be cleaved by restriction enzyme digests. Other techniques for separating polynucleotides from a solid substrate following solid-phase synthesis are known to those of ordinary skill in the art. Any suitable technique may be used. The polynucleotides may be collected and stored or processed further such as by amplification with polymerase chain reaction (PCR).

Illustrative System and Device

Figure 4:
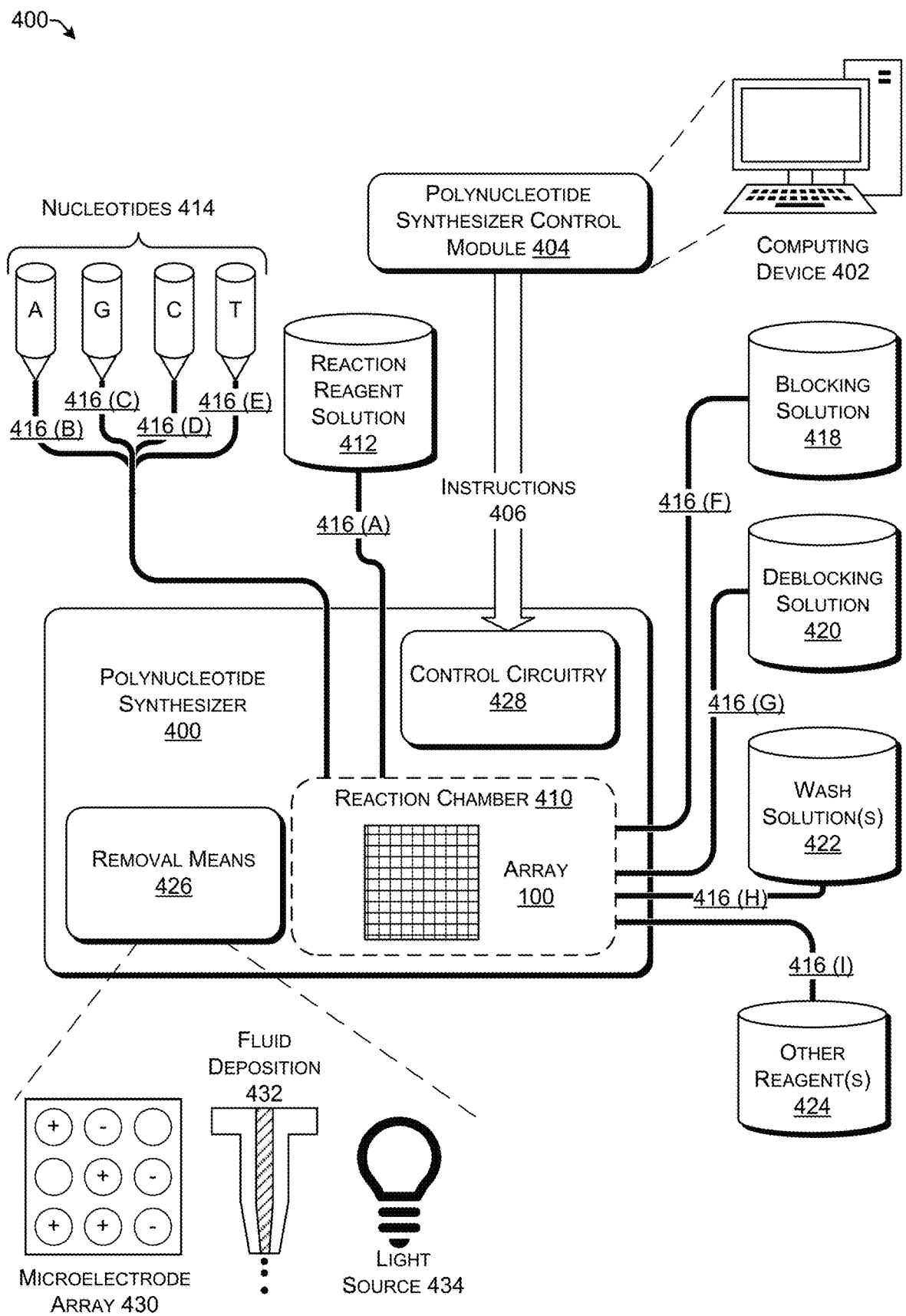
FIG. 4 shows an illustrative device for de novo synthesis of polynucleotides.

FIG. 4 is an illustrative system for implementing aspects of this disclosure. The system includes a device for de novo synthesis of polynucleotides that may be referred to as a polynucleotide synthesizer 400. The system may also include a computing device 402. The computing device 402 includes at least one or more processing units and memory such as random-access memory ("RAM") and/or read-only memory ("ROM") communicatively coupled to the processing units. The computing device 402 may also include a mass storage device configured to store files, documents, and data such as, for example, sequence data that is provided to the polynucleotide synthesizer 400 in the form of instructions. The computing device 402 may be implemented as any type of conventional computing device such as a desktop computer, a laptop computer, a server, a hand-held device, or the like. In an implementation, the computing device 402 may be a part of the polynucleotide synthesizer 400 rather than a separate device.

The computing device 402 may include a polynucleotide synthesizer control module 404. The polynucleotide synthesizer control module 404 provides instructions 406 that can control the operation of polynucleotide synthesizer 400. For example, the instructions 406 may communicate to the polynucleotide synthesizer 400 base sequences of polynucleotides for synthesis.

The polynucleotide synthesizer 400 is a device that performs automated solid-phase synthesis of polynucleotides on an array 100. The array 100 has a plurality of initiators attached thereto and may be located within a reaction chamber 410 configured to maintain an aqueous solution such as a reaction reagent solution 412 in contact with the surface of the array 100. The polynucleotide synthesizer 400 may also include a heater to raise the temperature of the aqueous solution in the reaction chamber 410. The polynucleotide synthesizer 400 may also include a cooling device such as a fan or thermoelectric cooler (e.g., Peltier device) to lower the temperature of the aqueous solution in the reaction chamber 410.

The array 100 may be formed from one or more of silicon dioxide, glass, an insoluble polymer, a non-reactive metal such as gold, silver, or platinum, or other material. The array 100 may be an electrochemically inert surface or it may include a plurality of spatially addressable microelectrodes. Thus, in an implementation, the array 100 may be a microelectrode array with individually addressable electrodes.

The polynucleotide synthesizer 400 may also include storage tanks, bottles, vials, or other containers or receptacles for storing solutions and reagents used in the synthesis of polynucleotides collectively referred to as reservoirs. One such reservoir may contain or be configured contain the reaction reagent solution 412. The reaction reagent solution 412 is an aqueous solution that contains a template-independent polymerase, metal cofactors for the polymerase, and at least one of a salt or buffer. For example, the reaction reagent solution 412 may contain 0.2 M potassium cacodylate, 0.025 M Tris, 0.01% (v/v) Triton X-100, 1 mM $CoCl_2$ in DI water.

The buffer may be any one of a number of known aqueous buffers that are compatible with polymerases such as, for example, PBS. PBS is a water-based salt solution containing disodium hydrogen phosphate, sodium chloride, and, in some formulations, may also include one or more of potassium chloride and potassium dihydrogen phosphate. Other examples of aqueous buffers known to those of ordinary skill in the art include HEPES, MOPS, PBST, TAE, TBE, TBST, TE, and TEN. See Vincent S. Stoll & John S. Blanchard, *Buffers: Principles and Practice,* 182 Meth. Enzoml., 24 (1990).

Nucleotides 414 may be stored separately in different reservoirs. Each species of nucleotide may be stored in a separate reservoir. If synthesizing DNA, the nucleotides 414 may be dNTPs that include one of the natural bases adenine (A), guanine (G), cytosine (C), or thymine (T). If synthesizing RNA, the nucleotides 414 may be NTPs that include one of the natural bases adenine (A), guanine (G), cytosine (C), or uracil (U). In an implementation, the nucleotides are unmodified nucleotides. In an implementation, the nucleotides are 3'-OH modified nucleotides that include a 3' blocking group.

Although four different types of nucleotides 414 are illustrated in FIG. 4, the polynucleotide synthesizer 400 may include fewer types (e.g., omit one of the standard nucleotides) or more types (e.g., include one or more artificial nucleotides). Only one species of nucleotide is provided during each cycle of synthesis to control which nucleotide is next incorporated by the template-independent polymerase into the polynucleotides. However, different ones of the available nucleotides 414 may be introduced during different cycles of synthesis to create a plurality of polynucleotides at different locations each with a different nucleotide sequence.

Both the reaction reagent solution 412 and the nucleotides 414 may be brought into contact with the array 100 by a fluid delivery pathway 416 that has a fluid connection with the reaction chamber 410. A first fluid delivery pathway 416(A) may deliver the reaction reagent solution 412 to the reaction chamber 410. A second fluid delivery pathway 416(B) may deliver a selected species of nucleotide 414 to the reaction chamber 410. A third fluid delivery pathway 416(C), fourth fluid delivery pathway 416(D), fifth fluid delivery pathway 416(E) and so on may deliver other species of nucleotides 414 to the reaction chamber 410.

The fluid delivery pathways 416 may be implemented by one or more of tubes and pumps, microfluidics, laboratory robotics, syringe systems, inkjet systems, manual pipetting, or other techniques that move controlled volumes of fluids from one location to another. The fluid delivery pathways 416 may also be implemented as flow cells, flow channels, or microfluidic channels which can deliver separate reagents or a mixture of reagents or washes using pumps or electrodes or other methods known to those of skill in the art through one or more channels to the reaction chamber. Such these and other devices and methods of moving fluid reagents are known to those of skill in the art. The fluid delivery pathways 416 are configured to contact the array 100 with the liquid contained in one of the reservoirs.

A blocking solution 418 or appropriate reservoir configured for holding the blocking solution 418 which may be included in the polynucleotide synthesizer 400. The blocking solution 418 contains 3' blocking groups, or a chemical that will convert to 3' blocking groups, which attach to 3'-OH groups on the plurality of initiators on the array 100. The blocking solution 418 may be an aqueous solution prepared with, for example, DI water.

Any number of suitable buffers known to those of ordinary skill in the art may be used in the blocking solution. For example, the blocking solution may be buffered with sodium hydroxide or tris buffer. The blocking solution may be adjusted to a pH from about 7-9 such as a pH of about 8. The blocking solution may be an acylation solution that adds acyl groups such as acyl groups to the 3'-OH groups on the initiators. Thus, attaching 3' blocking groups to the plurality of initiators may be accomplished by acylating the 3'-OH groups on the plurality of initiators. The acylation solution may comprise about 1 M acyl imidazole buffered with sodium hydroxide or tris buffer to a pH of about 8. The reservoir configured to hold the blocking is connected to the reaction chamber 410 by a fluid delivery pathway 416(F).

A deblocking solution 420 or appropriate reservoir configured for holding the deblocking solution 420 may be included in the polynucleotide synthesizer 400. The deblocking solution 420 may be an electrolyte solution. Alternatively, the deblocking solution may not necessarily contain electrolytes but may contain photobases to generate base upon exposure to a light source. In an implementation, the deblocking solution is a deacylation solution. The deacylation solution may comprise about 50 mM potassium phosphate buffer adjusted to a pH of about 7.4. The reservoir configured to hold the deblocking is connected to the reaction chamber 410 by a fluid delivery pathway 416(G).

One or more wash solutions 422 or appropriate reservoir(s) configured for holding the wash solution(s) 422 may be included in the polynucleotide synthesizer 400. The wash solution(s) 422 may be any of the wash solutions described in connection with operation 304, operation 310, or operation 314 shown in FIG. 3. The wash solution(s) 422 may be water (e.g., DI water) or an aqueous solution that contains at least one of a salt or a buffer. The salt or the buffer may be the same as the salt or buffer used in the reaction reagent solution 412. Alternatively, the salt or the buffer may be a different salt or buffer that is suitable for washing polynucleotides such as PBS or TBS. The wash solution(s) 422 may contain a surfactant such as a, for example, 1% solution of sodium dodecyl sulfate. The wash solution(s) 422 may contain a protease such as Proteinase K. The reservoir configured to hold the wash solution is connected to the reaction chamber 410 by a fluid delivery pathway 416(G).

The wash solution 422 is flowed into the reaction chamber 410 through a fluid delivery pathway 416(F). The wash solution 422 displaces the template-independent polymerase and any free nucleotides 414 in the reaction chamber 410. By removing any free nucleotides 414, the subsequent cycle of polymerization can introduce a different species of nucleotide without contamination from the previous cycle. Multiple cycles of addition of the same nucleotide 414 are possible and may each be followed by a wash step even though the same species of nucleotide is being added.

One or more other reagents 424 may also be included in the polynucleotide synthesizer 400 and brought into contact with the array 100 through a fluid delivery pathway 416(I). The other reagents 424 may include, for example, an acid, a base, a metal cofactor, or a support electrolyte.

As discussed above, there are multiple different devices and techniques for selectively removing 3' blocking groups from the initiators or polynucleotide strands at a selected location on an array 100. All of these different devices and techniques are referred to collectively as a removal means 426. The removal means 426 provides spatially-addressable removal of 3' blocking groups from a selected location on the array 100. The removal means 426 may be controlled by control circuitry 428 which directs the removal means 426 to remove 3' blocking groups from a specific region or regions on the array 100.

The control circuitry 428 may be implemented as any type of circuitry suitable for controlling hardware devices such as a printed circuit board, microcontroller, a programmable logic controller (PLC), or the like. The control circuitry 428 receives and acts on the instructions 406 provided by the polynucleotide synthesizer control module 404. Thus, the control circuitry 428 can cause the removal means 426 to remove the 3' blocking groups from initiators at the selected location on the array thereby controlling where polynucleotide strand extension occurs on the array 100. The control circuitry 428 may also control the fluid delivery pathways 416. For example, the control circuitry 428 may selectively open and close the various fluid delivery pathways 416 according to a preprogrammed sequence received in the instructions 406. Thus, the control circuitry 428 can also control the species of nucleotide 414 that is added during any cycle of synthesis.

In an implementation, the array 100 is a microelectrode array 430, the removal means 426 is the microelectrode array 430, and the control circuitry 428 may be configured to set the voltage independently at any (or all) of the electrodes in the microelectrode array 430 in any arbitrary pattern. The microelectrode array 430 may be any of the microelectrode arrays described in this disclosure. In an implementation, the microelectrode array 430 may be used to generate a negative voltage to create a localized basic environment on the surface of the array at the selected location. The voltage may be from about −1.4 V to about −2.0 V for example about −1.6 V.

The removal means 426 may be a targeted fluid deposition instrument 432 and the control circuitry 428 may control the location of a print nozzle and the type of reagent that is dispensed onto the surface of the array 100. Any of the reservoirs shown or described in connection with FIG. 4 may be sources of fluids for deposition by the targeted fluid deposition instrument 432. Thus, the control circuitry 428 may cause an acid or a base to be dispensed according to any arbitrary pattern across one or more selected locations on the array 100. This can create a localized acidic environment or a localized basic environment. The buffering capacity of the solution in contact with the array 100 controls the range over which the added acid or base affects pH. As the buffering capacity increases, the area of effect for added acid or base decreases and spatial control becomes more precise. In this implementation, the array 100 does not need to contain electrodes and may be an electrochemically inert surface.

The targeted fluid deposition instrument 432 may be implemented as any type of equipment or device that can precisely apply small volumes of chemical reagents to specific locations on the surface of the array 100. Examples include a chemical inkjet printing device or precision laboratory robotics. Chemical inkjet printing uses techniques similar to conventional printing to place nanoliter volumes of reagents at specified locations on a two-dimensional surface. Techniques for using inkjet printing to precisely deliver chemical reagents to selected locations on a surface of an array are well-known to those of ordinary skill in the art. See Paul Calvert, *Inkjet Printing for Materials and Devices,* 13(10) Chem. Mater. 3299 (2001).

Any type of chemical inkjet printing may be adapted for use with this disclosure. Inkjet printing can be divided into two categories: (1) drop-on-demand (DoD) or impulse inkjet, where droplets are generated when required; and (2) continuous inkjet, in which droplets are deflected from a continuous stream to a substrate when needed. Inkjet printing can be further subdivided according to the specific means of generating droplets, such as piezoelectric, thermal, and electrostatic. Droplet size involves, typically, volumes ranging from 1.5 pL to 5 nL at a rate of 0-25 kHz for drop-on-demand printers (and up to 1 MHz for continuous printheads).

Electrohydrodynamic jet printing (EHJP) is another printing technology that may be used. EHJP is a high-resolution printing technology where the printed liquid is driven by an electric field. Exposure to an electric field causes mobile ions in a polarizable liquid to accumulate at the liquid surface. Deposited droplets can be as small as 240 nm with spatial accuracy in the hundreds of nm, which is typically an order of magnitude smaller than other inkjet printing technologies. Such small droplet sizes dispense less material with more spatial control, which allows for more selectivity in controlling polymerase activity.

The removal means 426 may be directable light source 434 and the control circuitry 428 may turn the light source 434 on and off and control where light from the light source 434 contacts the array 100. Light from the light source 434 may be directed or focused on to the surface of the array 100 by optoelectronics such as a photomask or DMD (e.g., a DLP400 available from Texas Instruments). The duration of exposure depends on the specific photosensitive molecule and may be, for example, about 10, 20, 30, 40, 50, or 60 seconds. Thus, the removal means 426 as a light source 434 may be implemented as the light source 434 in conjunction with the optoelectronics. One example of a DMD that directs light onto an array surface is provided in Howon Lee et al. supra. The light source 434 generates light of a specific wavelength or range of wavelengths. Light from the light source 434 may be used to excite a photo-sensitive molecule such as a photobase or a photocleavable linker. In this implementation, the array 100 does not need to contain electrodes and may be an electrochemically inert surface.

In an implementation, light from the light source 434 activates a photobase and creates a localized basic environment at the selected location. The change in pH causes base-cleavable 3' blocking groups to separate from polynucleotide strands. In an implementation, light from the light source 434 cleaves a photocleavable linker attaching a 3' blocking group to the 3' end of a polynucleotide strand.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used in this document "or" means and/or. For example, "A or B" means A without B, B without A, or A and B. As used herein, "comprising" means including all listed features and potentially including addition of other features that are not listed. "Consisting essentially of" means including the listed features and potentially including additional features that do not materially affect the basic and novel characteristics of the listed features. "Consisting of" means only the listed features to the exclusion of any feature not listed.

Clause 1. A method for enzymatic synthesis of polynucleotides, the method comprising: a) attaching acyl groups to 3' ends of a plurality of initiators attached to a microelectrode array; b) incubating the microelectrode array in a deacylation solution; c) activating a subset of electrodes in the microelectrode array to generate a negative voltage at a selected location; d) incubating the microelectrode array with a single species of nucleotide and template independent polymerase; and e) contacting the array with a wash solution.

Clause 2. A method for enzymatic synthesis of polynucleotides, the method comprising: on an array having a plurality of initiators attached thereto, a) selectively removing 3' blocking groups from the initiators at a selected location on the array; b) incubating the array with a single species of nucleotide and template-independent polymerase; and c) contacting the array with a wash solution.

Clause 3. The method of clause 2, further comprising attaching the 3' blocking groups to the plurality of initiators on the array.

Clause 4. The method of clause 3, wherein attaching the 3' blocking groups to the plurality of initiators on the array comprises acylating 3'-OH groups on the plurality of initiators.

Clause 5. The method of clauses 1 or 4, wherein acylating the 3'-OH groups on the plurality of initiators comprises incubating the array with a solution comprising acyl imidazole and a buffer.

Clause 6. The method of any of clauses 1-5, wherein template-independent polymerase is TdT.

Clause 7. The method of any of clauses 1-6, wherein plurality of initiators comprises initiators having a length of between about 3-30 nucleotides.

Clause 8. The method of any of clauses 1-7, further comprising, after attaching the 3' blocking groups to the plurality of initiators, washing the array with a second wash solution.

Clause 9. The method of any of clauses 1-8, wherein the single species of nucleotides comprise unmodified nucleotides and incubating the array with the single species of nucleotides and the template-independent polymerase is performed for a reaction time.

Clause 10. The method of clause 9, wherein the selected species of nucleotide is one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP).

Clause 11. The method of clause 2, wherein selectively removing the 3' blocking groups comprises creating a localized basic environment at the selected location.

Clause 12. The method of 11, wherein the 3' blocking groups comprise acyl groups and selectively removing the 3' blocking groups comprises deacylating the initiators.

Clause 13. The method of clause 1 or 12, wherein the acyl group is an acetyl group.

Clause 14. The method of clause 11, wherein the localized basic environment is created by a voltage generated at an electrode and further comprising before deacylating the initiators at the selected location: contacting the array with deacylation solution comprising a buffer at a pH between about 4-10.

Clause 15. The method of clause 11, wherein the localized basic environment is created by a voltage generated at an electrode and the voltage is about −1.4 to −2.0 V.

Clause 16. The method of clause 11, wherein the localized basic environment is created by a photobase activated by exposure to a light source.

Clause 17. The method of clause 11, wherein the localized basic environment is created by a base applied by a targeted fluid deposition device.

Clause 18. The method of any of clauses 2-10, wherein: the 3' blocking groups are acid-cleavable and selectively removing the 3' blocking groups comprises creating a localized acidic environment at the selected location, or the 3' blocking groups are photocleavable and selectively removing the 3' blocking groups comprises exposing the selected location to a light source.

Clause 19. The method of any of any of clauses 1-8 or 11-18, wherein the template-independent polymerase is a modified template independent polymerase capable of incorporating 3'-OH modified nucleotides and the single species of nucleotide comprises 3'-OH modified nucleotides.

Clause 20. The method of clause 19, wherein the 3'-OH modified nucleotides comprise 3'-O-acetyl modified nucleotides.

Clause 21. The method of any of clauses 1-8 or 11-18, wherein the single species of nucleotide comprises nucleotides tethered to the template-independent polymerase.

Clause 22. The method of clause 1, further comprising repeating steps a)-e) while changing both the selected location and the species of nucleotide each at least once.

Clause 23. The method of clause 2, further comprising repeating steps a)-c) while changing both the selected location and the species of nucleotide each at least once.

Clause 24. A device for de novo synthesis of polynucleotides, the device comprising: an array having a plurality of initiators attached thereto; a first fluid delivery pathway configured to contact the array with a blocking solution comprising 3' blocking groups which attach to 3'-OH groups on the plurality of initiators; a second fluid delivery pathway configured to contact the array with a reaction reagent solution comprising a template-independent polymerase; a third fluid delivery pathway configured to contact the array with a selected species of nucleotide; a fourth fluid delivery pathway configured to contact the array with a wash solution; a removal means for addressable removal of 3' blocking groups at a selected location on the array; and control circuitry configured to: selectively open the first fluid delivery pathway, the second fluid delivery pathway, the third fluid delivery pathway, and the fourth fluid delivery pathway and to cause the removal means to remove the 3' blocking groups from initiators at the selected location on the array.

Clause 25. The device of clause 24, wherein the array comprises a microelectrode array, the removal means comprises the microelectrode array, the blocking solution comprises an acylation solution comprising acyl imidazole, the 3' blocking groups comprise acyl groups, and the control circuitry is configured to cause the microelectrode array to generate a negative voltage at the selected location on the array.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents, and/or patent applications throughout this specification. Each of the cited references is individually incorporated herein by reference for its particular cited teachings as well as for all that it discloses.

The invention claimed is:

1. A method for enzymatic synthesis of polynucleotides, the method comprising:
   on a microelectrode array having a plurality of initiators attached thereto,
   a) designing a sequence of nucleotide bases that encodes digital information;
   b) selectively removing 3' blocking groups from the initiators at a selected location on the microelectrode array by activating a subset of individually addressable electrodes in the microelectrode array, wherein selectively removing the 3' blocking groups comprises creating a localized basic environment at the selected location and wherein the localized basic environment is created by a voltage generated at an electrode;
   c) incubating the microelectrode array with a single species of nucleotide and template-independent polymerase;
   d) contacting the microelectrode array with a wash solution; and
   e) repeating steps b)-d) until the sequence of nucleotide bases is synthesized at the selected location.

2. The method of claim 1, further comprising, prior to step a), attaching the 3' blocking groups to the plurality of initiators on the array.

3. The method of claim 2, further comprising, after attaching the 3' blocking groups to the plurality of initiators and prior to step a), washing the array with a second wash solution.

4. The method of claim 2, wherein attaching the 3' blocking groups to the plurality of initiators on the array comprises acylating 3'—OH groups on the plurality of initiators.

5. The method of claim 4, wherein acylating the 3'—OH groups on the plurality of initiators comprises incubating the array with a solution comprising acyl imidazole and a buffer.

6. The method of claim 1, further comprising repeating steps (b-d) while changing both the selected location and the species of nucleotide each at least once.

7. The method of claim 1, wherein the single species of nucleotide comprises unmodified nucleotides and incubating the array with the single species of nucleotide and the template-independent polymerase is performed for a reaction time.

8. The method of claim 1, wherein the 3' blocking groups comprise acyl groups and selectively removing the 3' blocking groups comprises deacylating the initiators.

9. The method of claim 1, wherein the localized basic environment is created by a voltage generated at an electrode and the voltage is about −1.4 to −2.0 V.

10. The method of claim 1, wherein the template-independent polymerase is a modified template independent polymerase capable of incorporating 3'-OH modified nucleotides and the single species of nucleotide comprises 3'-OH modified nucleotides.

11. The method of claim 10, wherein the 3'-OH modified nucleotides comprise 3'-O-acetyl modified nucleotides.

12. The method of claim 1, wherein the single species of nucleotide comprises nucleotides tethered to the template-independent polymerase.

13. The method of claim 1, prior to step b), contacting the array with a deacylation solution.

14. The method of claim 13, wherein the deacylation solution comprises a buffer at a pH between about 4-10.

15. A method for enzymatic synthesis of polynucleotides, the method comprising:
   on a microelectrode array having a plurality of initiators attached thereto,
   a) selectively removing 3' blocking groups from the initiators at the selected location on the microelectrode array by activating a subset of individually addressable electrodes in the microelectrode array, wherein selectively removing the 3' blocking groups comprises creating a localized basic environment at the selected location and wherein the localized basic environment is created by a voltage generated at an electrode;
   b) incubating the microelectrode array with a single species of nucleotide and template-independent polymerase; and
   c) contacting the microelectrode array with a wash solution,
   further comprising repeating steps a)-c) while changing both the selected location and the species of nucleotide each at least once, wherein the repeating steps a)-c) synthesizes a first polynucleotide at a first location on the array and a second polynucleotide at a second location on the array each with different sequences encoding different digital information.

* * * * *